US009664262B2

(12) United States Patent
Donlon et al.

(10) Patent No.: US 9,664,262 B2
(45) Date of Patent: May 30, 2017

(54) FORCE TRANSMISSION MECHANISM FOR TELEOPERATED SURGICAL SYSTEM

(71) Applicant: INTUITIVE SURGICAL OPERATIONS, INC., Sunnyvale, CA (US)

(72) Inventors: Edward P. Donlon, San Jose, CA (US); Theodore W. Rogers, Alameda, CA (US); Bram Lambrecht, Mountain View, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 293 days.

(21) Appl. No.: 14/277,000

(22) Filed: May 13, 2014

(65) Prior Publication Data

US 2014/0338477 A1 Nov. 20, 2014

Related U.S. Application Data

(60) Provisional application No. 61/823,688, filed on May 15, 2013.

(51) Int. Cl.
*F16H 19/02* (2006.01)
*A61B 34/30* (2016.01)
*A61B 17/00* (2006.01)

(52) U.S. Cl.
CPC .............. *F16H 19/02* (2013.01); *A61B 34/30* (2016.02); *A61B 2017/00477* (2013.01); *Y10T 74/18792* (2015.01)

(58) Field of Classification Search
CPC .......... F16H 19/02; F16H 21/08; F16H 21/04; F16H 21/44; F16H 25/08; F16H 25/18; F16H 27/08; F16H 27/04; F16H 27/06; F16H 35/02; Y10T 74/18792; A61B 2017/00477; A61B 2017/00367; A61B 18/1442; A61B 18/1445; A61B 18/1447;
(Continued)

(56) References Cited

U.S. PATENT DOCUMENTS

| 5,395,369 A | 3/1995 | McBrayer et al. |
| 6,394,998 B1 | 5/2002 | Wallace et al. |

(Continued)

OTHER PUBLICATIONS

International Search Report and Written Opinion for Application No. PCT/US14/037921, mailed on Feb. 3, 2015, 15 pages.
(Continued)

*Primary Examiner* — Jocelin Tanner
(74) *Attorney, Agent, or Firm* — Jones Robb, PLLC

(57) ABSTRACT

A force transmission mechanism for a teleoperated surgical instrument may include a gear, a push/pull drive element, and a connection element. The push/pull drive element may be configured to transmit force to actuate an end effector of the surgical instrument and to rotate with a shaft of the surgical instrument when the shaft is rotated by the force transmission mechanism. The connection element may operatively couple the gear and the push/pull drive element. The connection element may be configured to convert rotational movement of the gear to a substantially linear movement of the push/pull drive element. The connection element may be configured to rotate with the push/pull drive element and relative to the gear.

24 Claims, 15 Drawing Sheets

(58) Field of Classification Search
CPC ........ A61B 2018/0145; A61B 17/0218; A61B 2017/2932; A61B 2017/2912; A61B 2017/2913; A61B 2017/2915; A61B 2017/2916; A61B 2017/2923; A61B 2017/2933; A61B 34/30; H01H 21/285; G05G 5/24; G05G 5/22; G05G 5/18; B60T 7/101
See application file for complete search history.

(56) References Cited

U.S. PATENT DOCUMENTS

| | | | |
|---|---|---|---|
| 6,817,974 | B2 | 11/2004 | Cooper et al. |
| 6,817,998 | B2 | 11/2004 | LaHaye |
| 7,691,098 | B2 | 4/2010 | Wallace et al. |
| 7,963,913 | B2 | 6/2011 | Devengenzo et al. |
| 8,545,515 | B2 | 10/2013 | Prisco et al. |
| 2011/0071544 | A1* | 3/2011 | Steger ............... A61B 1/00149 606/130 |
| 2011/0295269 | A1 | 12/2011 | Swensgard et al. |

OTHER PUBLICATIONS

Ball and Shanks Fittings, Motion Control Technologies Incorporated, 4 pages, [online], [retrieved May 14, 2014]. Retrieved from the Internet: <URL: http://www.hellotrade.com/motion-control-technologies-incorporated/ball-shanks-fittings.html>.

Ball and Strap Fittings, Carl Stahl Sava Industries, Inc., 2 pages, [online], [retrieved May 14, 2014]. Retrieved from the Internet: <URL: http://www.savacable.com/pages/prod_02_03.html>.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

\* cited by examiner

FORCE TRANSMISSION MECHANISM FOR TELEOPERATED SURGICAL SYSTEM

This application claims the benefit of U.S. Provisional Application No. 61/823,688, filed on May 15, 2013, which is incorporated by reference herein in its entirety.

TECHNICAL FIELD

Aspects of the present disclosure relate to a force transmission mechanism with a connection permitting rotation and translational movement of a push/pull rod. Aspects of the present disclosure also relate to a teleoperated surgical system that has a force transmission mechanism with a connection permitting rotation and translational movement of a push/pull rod.

INTRODUCTION

Benefits of minimally invasive surgery are well known, and they include less patient trauma, less blood loss, and faster recovery times when compared to traditional, open incision surgery. In addition, the use of teleoperated surgical systems (e.g., robotic systems that provide telepresence), such as the da Vinci® Surgical System manufactured by Intuitive Surgical, Inc. of Sunnyvale, Calif. is known. Such teleoperated surgical systems may allow a surgeon to operate with intuitive control and increased precision when compared to manual minimally invasive surgeries.

Teleoperated surgical systems may include one or more surgical instruments or tools. To perform actions directed by a surgeon, the teleoperated surgical system may use connections that permit motion of a surgical instrument, or a component on which a surgical instrument is mounted, in more than one direction. In other words, the connection may be used to provide more than one degree of freedom for the motion of a surgical instrument. Further, the connection may be used to translate motive force from an actuator to the medical instrument or to a component to which the instrument is mounted. Thus, a connection may be required to provide different functions and movements, even if these functions and movements may otherwise conflict with one another from a mechanical or structural sense.

SUMMARY

Exemplary embodiments of the present disclosure may solve one or more of the above-mentioned problems and/or may demonstrate one or more of the above-mentioned desirable features. Other features and/or advantages may become apparent from the description that follows.

In accordance with at least one exemplary embodiment, a force transmission mechanism for a teleoperated surgical instrument may comprise a gear, a push/pull drive element, and a ball element. The gear may be configured to be driven by a drive input mechanism. The push/pull drive element may be configured to transmit force to actuate an end effector of the surgical instrument. The ball element may operatively couple the gear and the push/pull drive element, wherein driven motion of the gear is transmitted to the push/pull drive element to actuate the end effector.

In accordance with at least one exemplary embodiment, a force transmission mechanism for a teleoperated surgical instrument may comprise a gear, a push/pull drive element, and a connection element. The push/pull drive element may be configured to transmit force to actuate an end effector of the surgical instrument and to rotate with a shaft of the surgical instrument when the shaft is rotated by the force transmission mechanism. The connection element may operatively couple the gear and the push/pull drive element. The connection element may be configured to convert rotational movement of the gear to a substantially linear movement of the push/pull drive element. The connection element may be configured to rotate with the push/pull drive element and relative to the gear.

In accordance with at least one exemplary embodiment, a surgical instrument for a teleoperated surgical system comprises a shaft, an end effector disposed at a distal portion of the shaft, and a force transmission mechanism disposed at a proximal portion of the shaft. The force transmission mechanism may comprise a gear, a push/pull drive element, and a connection element. The gear may be configured to be driven by a drive input mechanism. The push/pull drive element may extend along the shaft to the end effector. The push/pull drive element may be configured to transmit force to actuate the end effector. The connection element may operatively couple the gear and the push/pull drive element to convert rotational movement of the gear to a substantially linear movement of the push/pull drive element to actuate the end effector. The connection element may be configured to rotate with the push/pull drive element and relative to the gear.

Additional objects, features, and/or advantages will be set forth in part in the description which follows, and in part will be obvious from the description, or may be learned by practice of the present disclosure and/or claims. At least some of these objects and advantages may be realized and attained by the elements and combinations particularly pointed out in the appended claims.

It is to be understood that both the foregoing general description and the following detailed description are exemplary and explanatory only and are not restrictive of the claims; rather the claims should be entitled to their full breadth of scope, including equivalents.

BRIEF DESCRIPTION OF THE DRAWINGS

The present disclosure can be understood from the following detailed description, either alone or together with the accompanying drawings. The drawings are included to provide a further understanding of the present disclosure, and are incorporated in and constitute a part of this specification. The drawings illustrate one or more exemplary embodiments of the present teachings and together with the description serve to explain certain principles and operation. In the drawings.

DETAILED DESCRIPTION

Aspects of the embodiments herein are described primarily in terms of an implementation using a da Vinci® Surgical System (specifically, a Model IS3000, marketed as the da Vinci® Si™ HD™ Surgical System), manufactured by Intuitive Surgical, Inc. of Sunnyvale, Calif. Knowledgeable persons will understand, however, that inventive aspects disclosed herein may be embodied and implemented in various ways, including teleoperated and non-teleoperated embodiments and implementations. Implementations on da Vinci® Surgical Systems (e.g., the Model IS3000; the Model IS2000, marketed as the da Vinci® Si™ HD™ Surgical System) are merely exemplary and are not to be considered as limiting the scope of the inventive aspects disclosed herein.

Various exemplary embodiments of the present disclosure contemplate a teleoperated surgical system having a force transmission mechanism with a connection permitting rotation and translational movement of a push/pull rod or wire. Exemplary embodiments of the present disclosure also contemplate a force transmission mechanism for a teleoperated surgical system, the force transmission mechanism having a connection permitting rotation and translational movement of a push/pull rod or wire in a surgical instrument.

Figure 1:
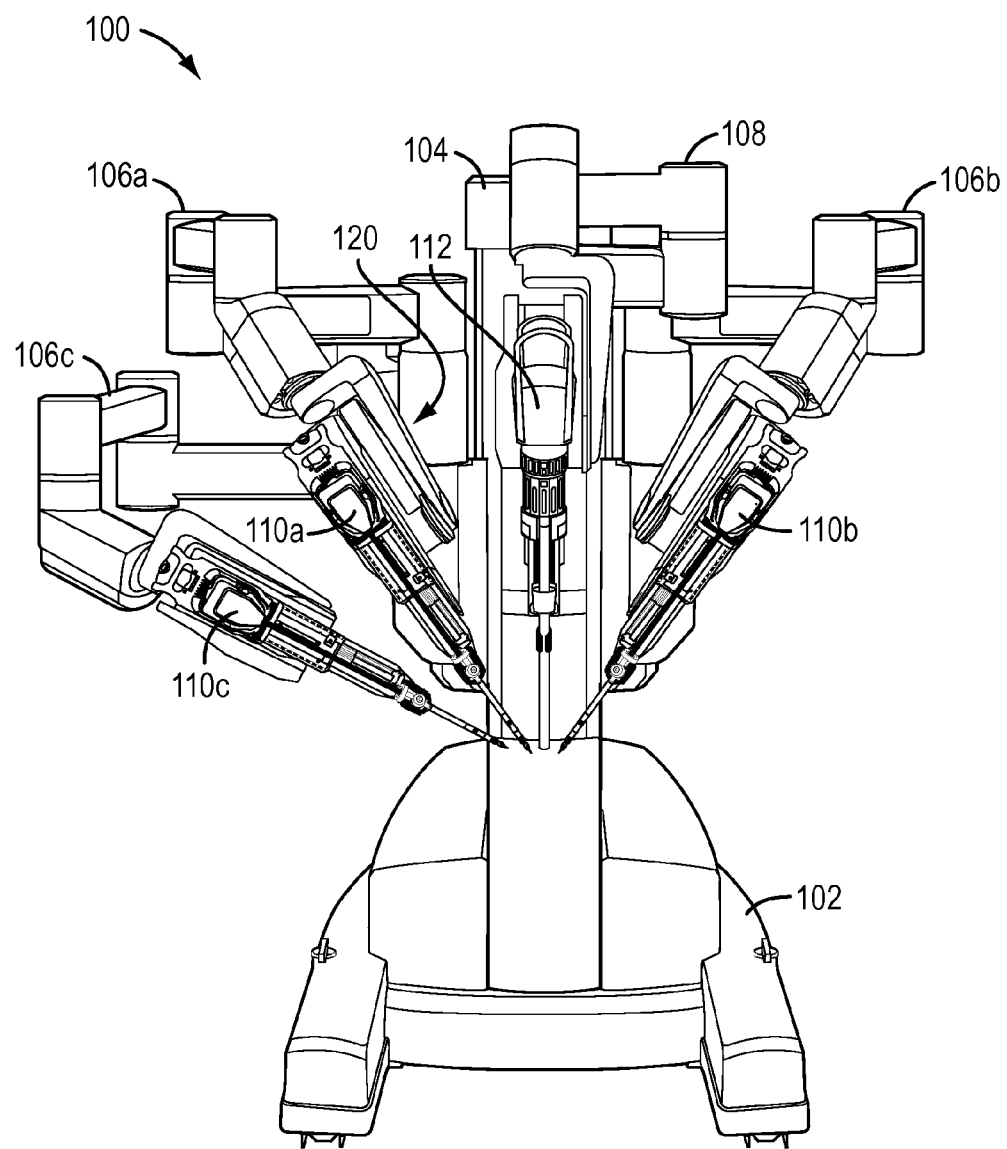
FIG. 1 is a front view of an exemplary embodiment of a patient side cart in a teleoperated surgical system.

FIG. 1 is a front view of the patient side cart component 100 of a teleoperated surgical system. A teleoperated surgical system allows a surgeon, with the assistance of a surgical team, to perform diagnostic and corrective surgical procedures on a patient. Such a teleoperated surgical system is described in U.S. Pat. No. 8,545,515, published Oct. 1, 2013, which is hereby incorporated by reference in its entirety. The patient side cart includes a base 102 that rests on the floor, a support tower 104 that is mounted on the base 102, and several arms that support surgical tools (which include a stereoscopic endoscope). According to an exemplary embodiment, surgical tools may be arranged according to the embodiments described in U.S. Pat. No. 6,817,974, published Nov. 16, 2004, and U.S. Pat. No. 6,394,998, published May 28, 2002, which are hereby incorporated by reference in their entirety.

As shown in FIG. 1, arms 106a, 106b are instrument arms that support and move the surgical instruments used to manipulate tissue, and arm 108 is a camera arm that supports and moves the endoscope. FIG. 1 also shows an optional third instrument arm 106c that is supported on the back side of support tower 104 and that can be positioned to either the left or right side of the patient side cart as necessary to conduct a surgical procedure. FIG. 1 further shows interchangeable surgical instruments 110a, 110b, 110c mounted on the instrument arms 106a, 106b, 106c, and it shows an endoscope 112 mounted on the camera arm 108. A surgical instrument 110a may be mounted to an arm 106a via a manipulator portion 120 (patient side manipulator "PSM") that supports and moves the surgical instrument.

Figure 2:
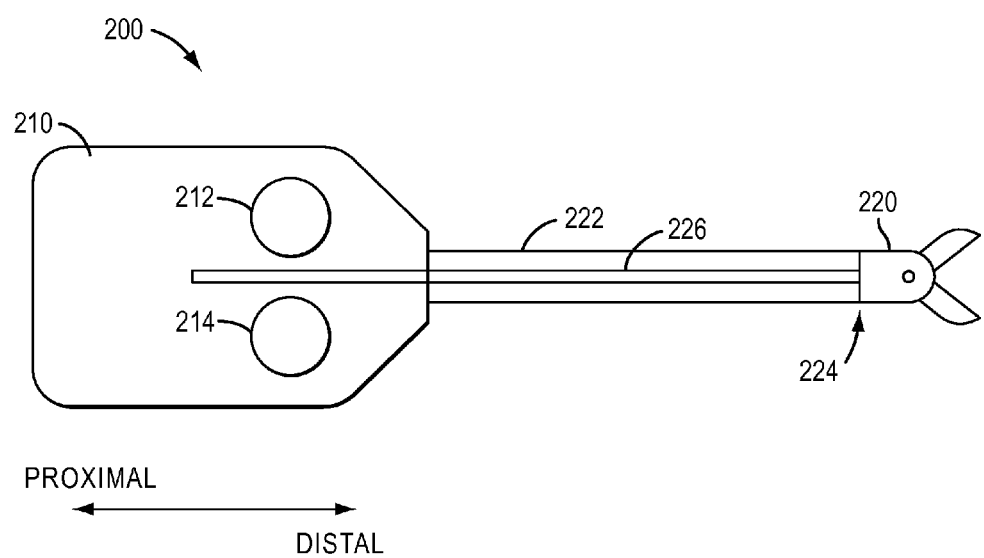
FIG. 2 is a top view of an exemplary embodiment of a surgical instrument including a force transmission mechanism.

FIG. 2 is a top view of an exemplary embodiment of a surgical instrument 200. Surgical instrument 200 may include a force transmission mechanism 210, an end effector 220 at a distal end 224 of the surgical instrument, and a shaft 222 connecting force transmission mechanism 210 and end effector 220. Surgical instrument 200 may include one or more members to translate force between force transmission mechanism 210 and end effector 220. For instance, one or more member(s) 226 may connect force transmission mechanism 210 to end effector 220 to provide actuation forces to end effector 220, such as by extending through an interior of shaft 222. By utilizing member(s) 226, force transmission mechanism 210 may actuate end effector 220 to, for example, control a wrist mechanism of instrument 200 and/or to control a jaw of end effector 220 (or other moveable part). Further, because end effector 220 may be fixed to shaft 222, force translated from force translation mechanism 210 to end effector 220 may in turn be translated to shaft 222, such as when force translation mechanism 210 actuates end effector 220 in a rolling motion.

Member(s) 226 may be in the form of tension elements, such as when force transmission mechanism 210 is a pull-pull mechanism, or one or more force isolation rods, such as when force transmission mechanism 210 is a push-pull mechanism, such as a drive rod element, as described in U.S. Pat. No. 8,545,515, published Oct. 1, 2013, which is incorporated by reference herein.

Force transmission mechanism 210 may include one or more components to engage with a patient side cart 100 to translate a force provided by patient side cart to surgical instrument 200. According to an exemplary embodiment, force transmission mechanism 210 may include one or more interface disks 212, 214 that engage with a PSM 120 of a patient side cart 100. Thus, interface disks 212, 214 may couple with actuators (e.g., servomechanisms) (not shown) in PSM 120 and translate a force from the actuators (e.g., servomechanisms) to surgical instrument 200. Thus, interface disks 212, 214 utilize the actuation forces from PSM 120 to actuate instrument 200. For instance, first disk 212 may be configured to provide a rolling motion to shaft 222 and provide a roll DOF for end effector 220, while second disk 214 may operate a jaw mechanism of end effector 220 to open and close.

The force transmission mechanism of FIG. 2 provides an accurate translation of rotational and translation movement of a control element to a surgical instrument of a teleoperated surgical system. However, such force transmission mechanisms require many moving parts and intermeshed elements, increasing manufacturing costs and making maintenance and cleaning more difficult, potentially limiting the number of times such an element may be used. It may be desirable to provide a force transmission mechanism that includes a connection permitting both rotational and translational movement of a push/pull drive element rod, while advantageously using fewer parts and providing a lower manufacturing cost. In addition to reducing costs, reducing the number of parts may improve the cleaning efficiency of the force transmission mechanism.

Figure 3:
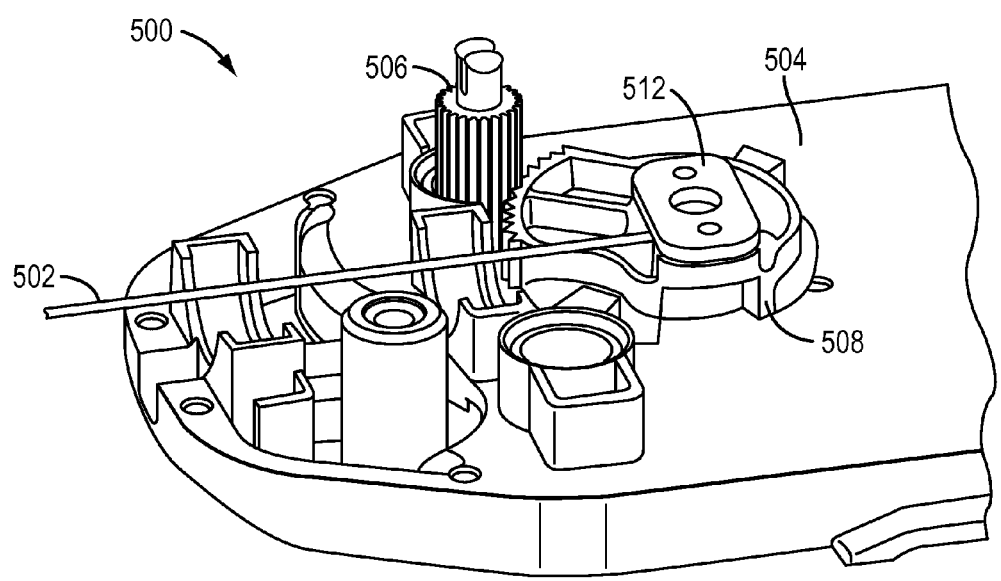
FIG. 3 is a perspective view of an exemplary embodiment of a force transmission mechanism used in a push/pull instrument design in accordance with the present teachings.

Turning to FIG. 3, an exemplary embodiment is shown of a force transmission mechanism 500 used in a push/pull instrument design for a teleoperated surgical system. Force transmission mechanism 500 may include features of the force transmission embodiments discussed above, including the features of the force transmission mechanism of the embodiments described in U.S. Pat. No. 8,545,515, published Oct. 1, 2013, which is incorporated by reference herein. For instance, force transmission mechanism 500 may include an input or interface disk 506 that may interface with another device to provide force or motion to an instrument, such as by coupling with an actuator (e.g., servomechanism) of a PSM, such as, for example, a carriage of a PSM. For instance, input disk 506 may provide a translational movement for the end effector, such as to open and close a jaw mechanism of the end effector, and a second input or interface disk (not shown) may provide a rotational movement to a shaft (not shown), as will be discussed below.

Force transmission mechanism 500 may include a base 504 to which components of the force transmission mechanism 500 may be mounted or attached. As shown in the exemplary embodiment of FIG. 3, a force transmission mechanism 500 may include an input disk 506. Input disk 506 may couple with an actuator (e.g., a servomechanism), such as, for example, a force transmission disk of a carriage of PSM 120 to couple actuation forces from actuators (e.g., servomechanisms) in PSM 120.

Force transmission mechanism 500 may further include a gear 508, as shown in the exemplary embodiment of FIG. 3. The gear 508 may be a gear having a geometry or configuration useful for saving space within the force transmission mechanism 500. According to an exemplary embodiment, gear 508 may be a sector gear 508. For ease of reference, gear 508 will be referred to as a sector gear 508, although other gear configurations may be used.

A sector gear 508 may require less space and require fewer parts than other gear configurations. For instance, only a portion 507 of sector gear 508 may include teeth or other structure that engage with corresponding teeth or other structure of the input disk 506, as shown in the exemplary embodiment of FIG. 6, instead of an entire outer perimeter or circumference of the gear including teeth or other structure to engage with the input disk 506. Further, as will be discussed below, because sector gear 508 may include teeth or other engaging structure on only a portion 507 of the gear 508, the gear 508 may move through a limited amount of space within the force transmission mechanism 500 when the input disk 506 provides a torque to the sector gear 508. As a result, relatively little open space is required within the force transmission mechanism 500 to accommodate the rotational movement of the sector gear 508.

Sector gear 508 may be coupled or otherwise connected to a push/pull drive element rod 502, as shown in the exemplary embodiment of FIG. 3. Push/pull drive element rod 502 may be coupled to an end effector of a surgical instrument (not shown) so that pushing and pulling rod 502 may actuate the end effector. For instance, for a forceps end effector, pushing on push/pull drive element rod 502 may open the jaws of the forceps, while pulling on rod 502 may close the jaws. Similarly, pushing and pulling on the rod 502 would open and close the shears. According to an exemplary embodiment, an end effector coupled to push/pull drive element rod 502 may be arranged according to the exemplary embodiments described in U.S. Pat. No. 8,545,515, published Oct. 1, 2013, which is incorporated herein by reference.

According to an exemplary embodiment, sector gear 508 may be coupled to the input disk 506. As a result, when a rotational force is applied to the input disk 506, such as via an actuator (e.g., servomechanism), such as a carriage that couples actuation forces from the actuators of a PSM, the rotation of the input disk 506 may cause the sector gear 508 to rotate. However, as will be discussed below, the sector gear 508 may convert its rotational movement to a substantially linear movement of the rod 502. Further, as will be discussed below, the connection between the sector gear 508 and the rod 502 may permit rotational movement of the rod 502 in addition to a linear, translational movement of the rod 502.

Figure 4:
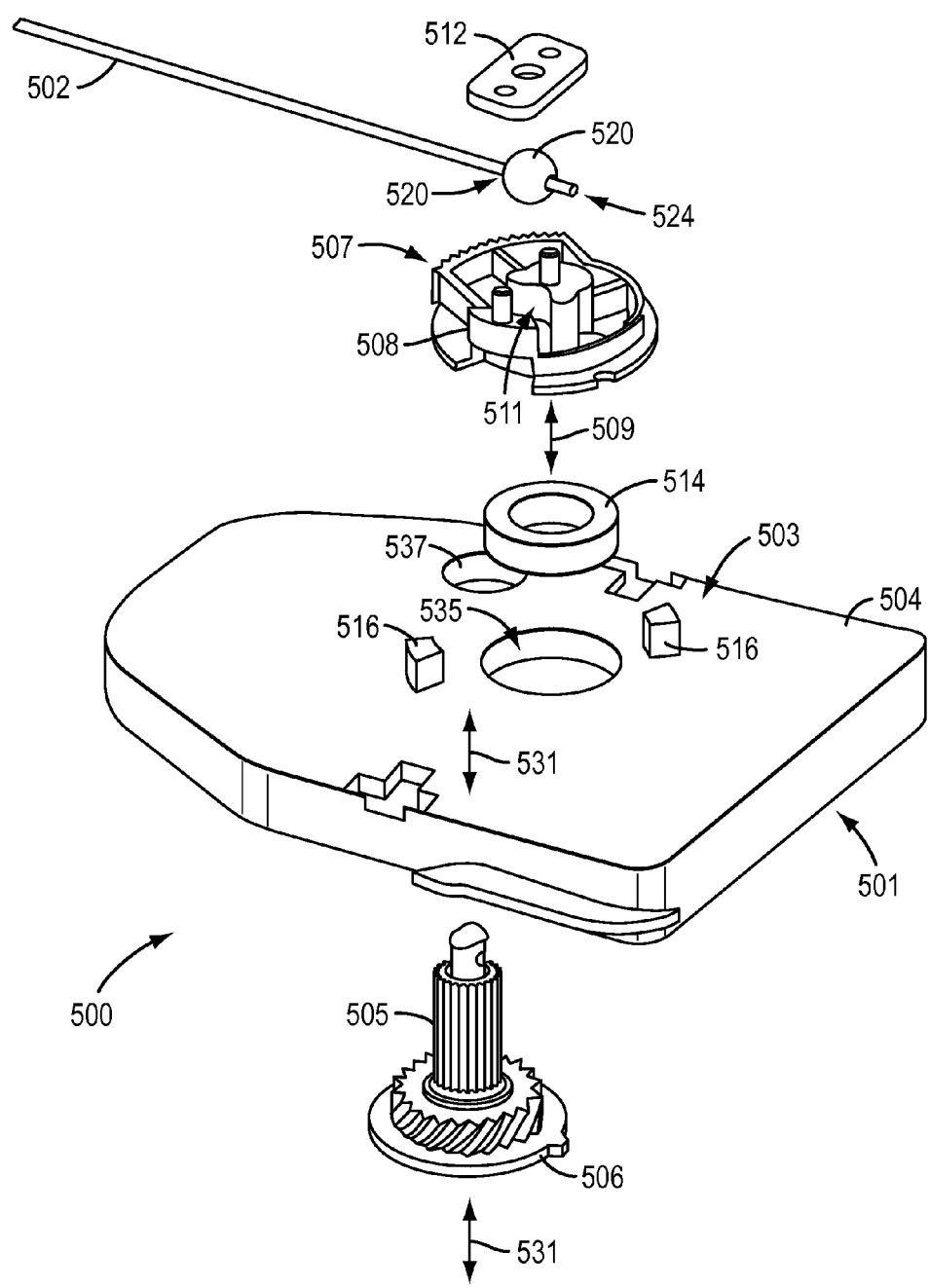
FIG. 4 is an exploded view of the force transmission mechanism of FIG. 3.

Turning to FIG. 4, an exploded perspective view of the force transmission mechanism 500 is shown to further illustrate features of the exemplary embodiment of the force transmission mechanism 500 shown in FIG. 3. As shown in FIG. 4, an input disk 506 may be inserted through an aperture 537 in the base 504 of the force transmission mechanism 500 so that the input disk 506 may engage with a sector gear 508. For instance, input disk 506 may include teeth 505 or other structure to engage with the portion 507 of sector gear 508 that includes teeth or other corresponding structure to engage the input disk 506 and the sector gear 508.

Components of the force transmission mechanism 500 may be configured to use a gear ratio from amongst a range of gear ratios. For instance, various gear ratios would be acceptable depending on a required torque and length of travel required for a specific instrument and/or end effector. Higher gear ratios may result in a larger amount of available torque and relatively lower amount of travel of a push/pull drive element rod, which may be advantageous for grasping. For instance, relatively large amounts of torque may be useful for grasping a suture needle or firing a clip. Lower gear ratios may result in lower available torque but a relatively large amount of travel for a push/pull drive element rod. According to an exemplary embodiment, a force transmission mechanism may employ gear ratios in a range of about 2:1 to about 8:1, depending upon a specific application of the force transmission mechanism. According to another embodiment, a force transmission mechanism may employ gear ratios in a range of about 3:1 to about 3.5:1. These gear ratios may be utilized by components of a force transmission mechanism and different components may use different gear ratios. In an exemplary embodiment in accordance with the present teachings, the engaging structures of input disk 506 and sector gear 508 may be structured to provide a gear ratio of, for example, approximately 5:1, such as approximately 60:12.

According to an exemplary embodiment, input disk 506 may be attached or otherwise mounted to a first side 501 or reverse side of the force transmission mechanism 500, while sector gear 508 is attached or otherwise mounted to a second side 503 or interior side of the force transmission mechanism 500. Portions of the sector gear 508 and the input disk 506 may engage one another via the aperture 537 in the base 504 of the force transmission mechanism 500.

According to an exemplary embodiment, a force transmission mechanism 500 may include one or more structures to support the sector gear 508. For instance, a force transmission mechanism 500 may include a bearing 514 located under a sector gear 508, as shown in FIG. 4. Bearing 514 may be inserted into a pocket 535 of the base 504, which may include a structure (not shown) to support the bearing 514 within aperture 535. For instance, the base 504 of the force transmission mechanism 500 may form a flange or ledge (not shown) within pocket 535 that the bearing 514 rests upon.

As discussed above, sector gear 508 may be connected to a push/pull drive element rod 502 so that when a torque is applied to sector gear 508 via input disk 506, the rotational movement of the sector gear 508 may be converted to a substantially linear movement of the rod 502, which may in turn actuate an end effector of a surgical instrument to which rod 502 is coupled. However, it may be desirable to provide the surgical instrument with a rotational degree of freedom substantially about longitudinal axis of the rod 502. As a result, it may be desirable for a connection between sector gear 508 and the push/pull drive element rod 502 to permit both conversion of the rotational movement of sector gear 508 to a substantially linear movement of rod 502 and to allow the rod 502 rotate freely with respect to the sector gear 508.

According to an exemplary embodiment, push/pull drive element rod 502 may be connected to sector gear 508 via a ball connection 520, as shown in FIG. 4. Ball connection 520 may have a shape of, for example, a substantially spherical ball with a hole 524 through the ball connection 520 that rod 502 may pass through, as indicated in FIG. 4. Hole 524 may, for example, substantially pass through a center of the ball connection 520 and be substantially the size of an outer diameter of the rod 502.

A size for the substantially spherical ball may be selected, for example, in order to balance available space within a force transmission mechanism, required force to be generated, and costs of the part(s). For instance, the ball may be relatively small to save cost and space within a force transmission mechanism. However, the ball should not be too small so that it is difficult to retain the ball within a force transmission mechanism. On the other hand, if the ball is relatively large, the ball may simply require additional cost and space without additional benefit. According to an exemplary embodiment, the ball may have a diameter of about 0.125 inches (about 3.175 mm) to about 0.5 inches (about 12.7 mm). According to another exemplary embodiment, the ball may have a diameter of about 0.25 inches (about 6.35 mm).

According to an exemplary embodiment, ball connection 520 may include one or more structures to affix the ball connection 520 to the push/pull drive element rod 502. Such structures may fix the position of the ball connection 520 relative to the length of the rod 502 so that when sector gear 508 provides a translational motion to rod 502 via ball connection 520, the rod 502 simply does not slide within the ball connection 520 but is pushed and pulled as a result of the ball connection 520.

Figure 5A:
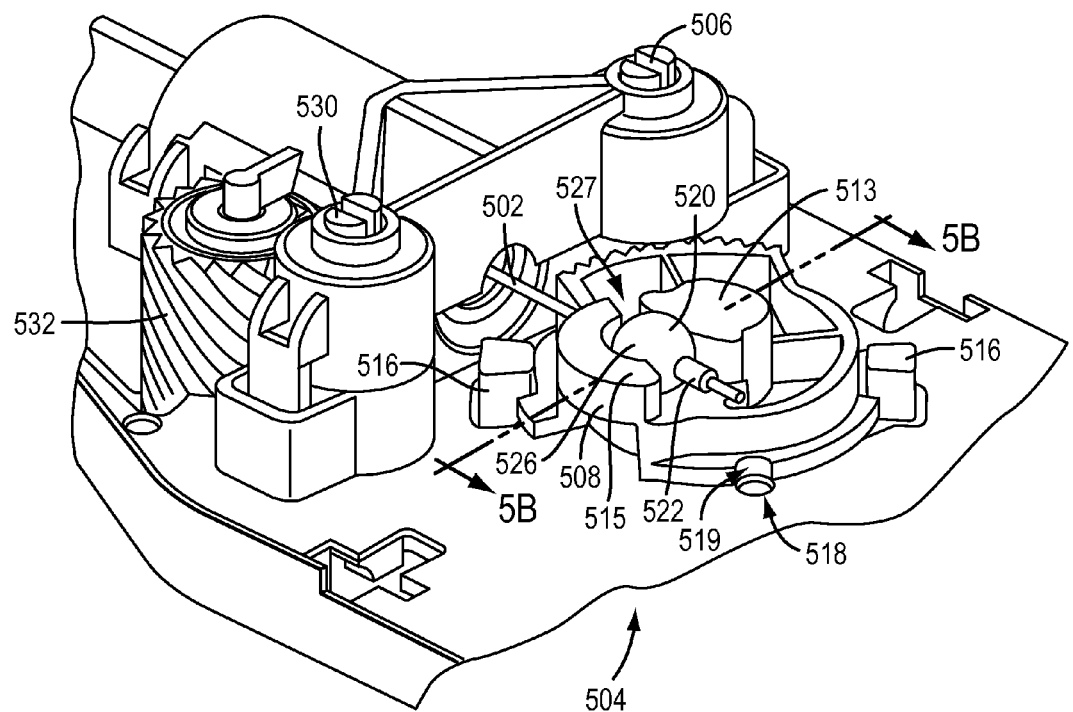
FIG. 5A is a perspective view an exemplary embodiment of a connection between a sector gear and ball connection of a force transmission mechanism in accordance with the present teachings.

Turning to FIG. 5A, which shows an enlarged view of an exemplary embodiment of an assembled connection between sector gear 508 and push/pull drive element rod 502, ball connection 520 may include one or more fasteners 522 that connect the ball connection 520 to the rod 502. A fastener 522 may be formed as a separate piece that is connected to or engaged with a ball element or portion 526 of the ball connection 520, via, for example, a weld, mechanical connection, or other joint used in the art, or fastener 522 and ball element 526 may be formed via a monolithic, single-piece construction. Thus, the hole 524 of a ball connection 520 may pass through and be formed by both a ball element 526 and one or more fasteners 522 of the ball connection 520.

According to an exemplary embodiment, fastener 522 may, for example, be substantially in the form of a cylinder that rod 502 passes through, as shown in FIG. 5A. After rod 502 has been inserted through the hole 524 of the ball connection 520, rod 502 may be fixed to ball connection 520 via the one or more fasteners 522. According to one exemplary embodiment, rod 502 may be fixed to fastener 522 by applying a force to fastener 522 to cause fastener 522 to deform and crimp about the rod 502 so that fastener 522 no longer moves relative to rod 502. In such an embodiment, fastener 522 may be referred to as a "crimp" due to the deformation of the fastener 522 upon the rod 502 to fix the fastener 522 to the rod 502. The method of joining the rod 502 to one or more fasteners 522 of a ball connection 520 is not limited to this embodiment and other methods may be used, such as, for example, via a weld, a threaded connection, adhesive, and other joining methods used in the art. Because the ball connection 520 (including the ball element 526 which is joined to fastener 522 or formed as a single, monolithic piece with fastener 522) is fixed to rod 502, whenever the sector gear 508 moves the ball connection 520 the ball connection 520 may in turn move rod 502.

Figure 6:
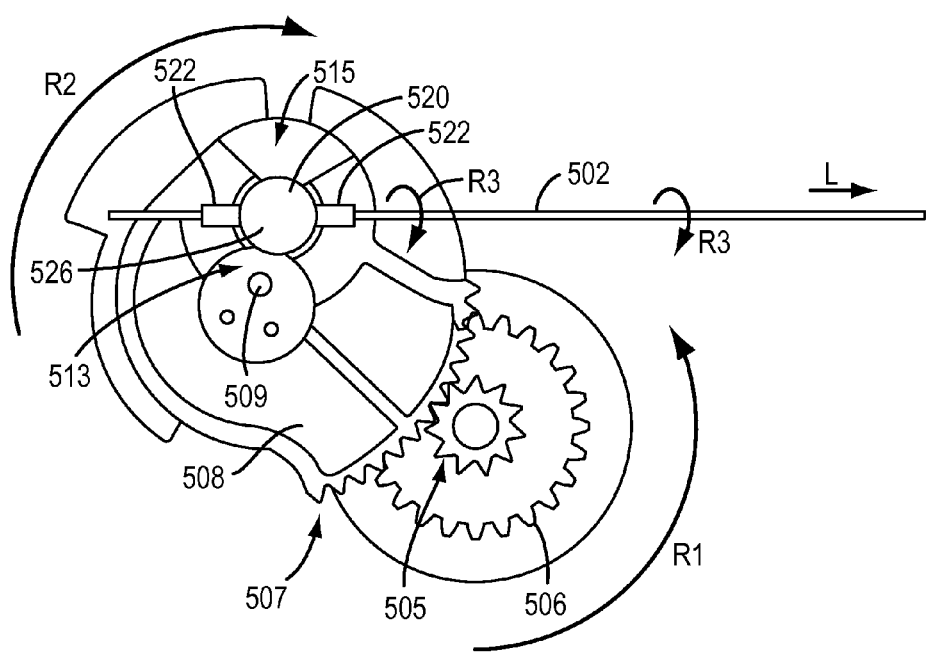
FIG. 6 is a top view showing an exemplary embodiment of connection between a sector gear, a ball connection, and a push/pull drive element rod when rotational movement is applied to the sector gear.

According to an exemplary embodiment, a ball connection 520 may include a plurality of fasteners 522. For instance, as shown in FIG. 6, a ball connection 520 may include a fastener 522 on each side of the ball element 526 of the ball connection 520 so that the ball connection 520 includes first and second fasteners 522 on opposite side of the ball element 526. Each fastener 522 may be fixed to rod 502 according to any of the methods described above, such as by crimping each fastener 522. The plurality of fasteners 522 may be formed as a monolithic, single piece construction with the ball element 526 of a ball connection 520 or may be separate pieces joined to the ball element 526, as described above. According to an embodiment, fasteners 522 may be provided as separate pieces from ball element 526, with each fastener 522 fixed to the rod 502 so that the ball element 526 is substantially held in place between the fasteners 522.

During assembly of a force transmission mechanism 500, it may be desirable to control the tolerances in a connection between a sector gear 508 and a push/pull drive element rod 502 so that a precise connection is made between the sector gear 508 and the rod 502. In particular, a force transmission mechanism 500 may be connected to a surgical instrument and the rod 502 of the force transmission mechanism 500 may be used to actuate an end effector of the surgical instrument. If a precise connection is not made between a rod 502 and a sector gear 508, the end effector may not be actuated according to the desires of a user. For instance, if the end effector is forceps, the forceps might not open or close fully because an imprecise connection between a rod 502 and a sector gear 508 does not provide a full range of motion for the forceps, such as when there is too much slack in the connection.

According to an exemplary embodiment, tolerances for a connection between a push/pull drive element rod 502 and a sector gear 508 of a force transmission mechanism 500 may be controlled or otherwise affected by controlling the location of where a ball connection 520 is fixed to the rod 502. For instance, during assembly of a force transmission mechanism 500, a push/pull drive element rod 502 may be inserted through a hole 524 of a ball connection 520 until the ball connection 520 is located at a point along an axial length of the rod 502 that will provide a precise connection to the rod 502. Once the ball connection 520 has been properly located along the axial length of a rod 502, the ball connection 520 may be fixed to the rod 502 at that location, such as via one or more fasteners 522, as discussed above. As a result, tolerances may be kept relatively small in the connection and the rod 502 may be used to actuate the end effector of a surgical instrument with relatively accurate movements. The ball connection 520 may further be connected to a sector gear 508, as will be explained below, to complete a connection between the rod 502 and the sector gear 508.

According to an exemplary embodiment, force transmission mechanism 500 may include one or more features to assist with assembly of the force transmission mechanism 500. For instance, as shown in FIG. 5A, a base 504 of the force transmission mechanism 500 may include an alignment aperture 518. During assembly, a key (not shown), such as a pin or other elongated structure, may be inserted through alignment aperture 518 and through an indentation 519 in the sector gear 508. As a result, the sector gear 508 may be temporarily prevented from rotating relative to the base 504. This may advantageously facilitate securing a ball connection 520 to the sector gear 508 by preventing the sector gear 508 from turning during the assembly process. Once the ball connection 520 has been secured to the sector gear 508, the key may be withdrawn from the indentation 519 and alignment aperture 518 to permit rotation of the sector gear 508.

According to an exemplary embodiment, a sector gear 508 may include one or more structures to connect a ball connection 520 to the sector gear 508. For instance, as shown in FIG. 5A, a sector gear 508 may include a socket 527 that the ball connection 520 is inserted into. Once placed within the socket 527, a ball connection 520 may be fixed to a sector gear 508 so that rotational movement of the sector gear may be converted by the ball connection 520 to a substantially linear movement of a rod 502 fixed to the ball connection, while permitting free rotation of the ball connection 520 within the socket 527.

According to an exemplary embodiment, an opening for socket 527 may be slightly smaller than a ball connection 520 so that the ball connection 520 may be secured within the socket 527 of the sector gear 508 by pressing the ball connection 520 through the opening of the socket 527 in a snap-fit type of arrangement. For instance, an opening of the socket 527 may be slightly smaller than a diameter of the ball element 526 of a ball connection 520.

Figure 5B:
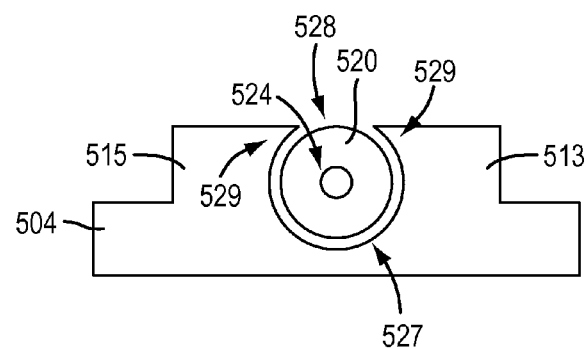
FIG. 5B is a cross-sectional view of an exemplary embodiment of a socket for a ball connection of a force transmission mechanism, as along line 5B-5B of FIG. 5A.

According to an exemplary embodiment, a socket 527 within a sector gear 508 for a ball connection 520 may be formed by one or more projections of the sector gear 508. For instance, as shown in the exemplary embodiment of FIG. 5A, a sector gear 508 may include projections 513, 515 that form a socket 527 between the projections 513, 515. According to an exemplary embodiment, projections 513, 515 may be formed with undercuts 529 to assist with securing a ball connection 520 within the socket 527, as shown in FIG. 5B. The undercuts 529 may form an opening 528 for the socket 527 that is slightly smaller than the ball connection 520, as shown in FIG. 5B, so that the ball connection 520 may be pressed through the opening 528 and secured within the socket 527. As shown in the exemplary embodiment of FIG. 5A, projections 513, 515 may be provided as discrete projections separate from one another and may be placed on opposite sides of a ball connection 520. According to another exemplary embodiment, a single, continuous projection (not shown) may be provided that forms an opening for a socket 527 and secures the ball connection 520 in place.

According to an exemplary embodiment, a ball connection 520 may be secured to a sector gear 508 by placing the ball connection within a recess of the sector gear 508 and then covering at least a portion of the ball connection 520. As shown in FIGS. 3 and 4, sector gear 508 may include a recess 511 that a ball connection 520 is inserted into and a plate 512 may be placed over at least a portion of the ball connection 520 to secure the ball connection 520 to the sector gear 508. The recess 511 may, for example, have a shape of a pit having an opening substantially the size of the ball connection 520, such as the ball element 526, with a bottom of the recess conforming in shape to the outer surface of the ball element 526. The plate 512 may be secured to the sector gear 508 by, for example, one or more mechanical fasteners, welds, adhesive, or other connections used in the art.

Connecting a ball connection 520 to a sector gear 508 via a plate 512 may be advantageous when greater forces are exerted between the sector gear 508, ball connection 520, and rod 502 because the plate may be able to withstand a greater pull-out force for the ball connection 520 than other connections, such as when only a socket 527 is provided with undercuts 529.

According to an exemplary embodiment, a ball connection 520 may be secured to a sector gear 508 using only a socket 527 according to the embodiments described above without further structures or assistance to connect the ball connection 520 to the sector gear 508. According to another exemplary embodiment, a ball connection 520 may be secured to a sector gear 508 such both a socket 527 and a plate 512, with each of the socket 527 and plate 512 arranged according to the exemplary embodiments described above.

A sector gear 508 may be secured to a base 504 of a force transmission mechanism 500 before or after a ball connection 520 is secured to the sector gear 508. As shown in the exemplary embodiment of FIGS. 4 and 5A, a sector gear 508 may be held to the base 504 by one or more tabs or flanges 516. Tabs 516 may be part of the base 504 and may be formed as a monolithic, single piece construction with base 504 or may be separate pieces joined to base 504. Tabs 516 may permit rotational movement of sector gear 508 relative to base 504, such as when input disk 506 imparts a rotational movement to sector gear 508. According to an exemplary embodiment, tabs 516 may include detent structures to engage with the sector gear 508 so that rotational movement of the sector gear 508 may be limited.

By providing a force transmission mechanism 500 with a ball connection 520, a compact connection may be advantageously provided between a push/pull drive element rod 502 and a sector gear 508 with fewer parts so that the push/pull drive element 502 and the sector gear 508 are operatively coupled. Further, because fewer parts are utilized, less space is used within the force transmission mechanism 500 for the parts connecting the sector gear 508 to a rod 502. For example, as described in U.S. application Ser. No. 12/618,583, filed on Nov. 13, 2009, published as U.S. Pub. No. 2011/0071542 on Mar. 24, 2011 a force transmission mechanism may include a gear connected to a drive element rod via a link, slider, and a rolling bearing.

In contrast, a force transmission mechanism 500 may be directly connected to a push/pull drive element rod 502 with a ball connection 520. According to an exemplary embodiment, a ball connection 520 may be directly connected to a sector gear 508. For instance, a ball connection 520 may be in direct contact with the sector gear 508, such as a socket 527 and/or a plate 512 of the sector gear 508. Further, a push/pull drive element rod 502 may be directly connected to a ball connection 520. For instance, the rod 502 may be in direct contact with the ball connection 520, including one or more fasteners 522 of the ball connection 520.

The efficient, compact connection between a push/pull drive element rod 502 and a sector gear 508 permits the push/pull drive element rod 502 and the sector gear 508 to be operatively coupled so a rotational motion of the sector gear 508 is converted into a substantially linear movement of the rod 502. Turning to FIG. 6, an exemplary embodiment of a connection is shown between a push/pull drive element rod 502, ball connection 520, and a sector gear 508. The remaining features of a force transmission mechanism 500 have been omitted in FIG. 6 for ease of viewing. As shown in FIG. 6, an input disk 506 may be engaged with the sector gear 508, such as via teeth 505 or other structure of input disk 506 that engage with the portion 507 of sector gear 508 that includes teeth or other corresponding structure, so that when a rotational movement is imparted to the input disk 506 in direction R1, around rotation axis 531 (shown in the exemplary embodiment of FIG. 4), the sector gear 508 may be rotated in direction R2 (around rotation axis 509 shown in the exemplary embodiment of FIG. 4). According to an exemplary embodiment, rotation axis 531 of input disk 506 and rotation axis 509 of sector gear 508 may be substantially parallel to one another. Because a push/pull drive element rod 502 is connected to the sector gear 508 via ball connection 520, when sector gear 508 rotates in direction R2, ball connection 520 is carried along by sector gear 508, causing rod 502 to be translated in a substantially linear direction L, as shown in FIG. 6.

Figure 7:
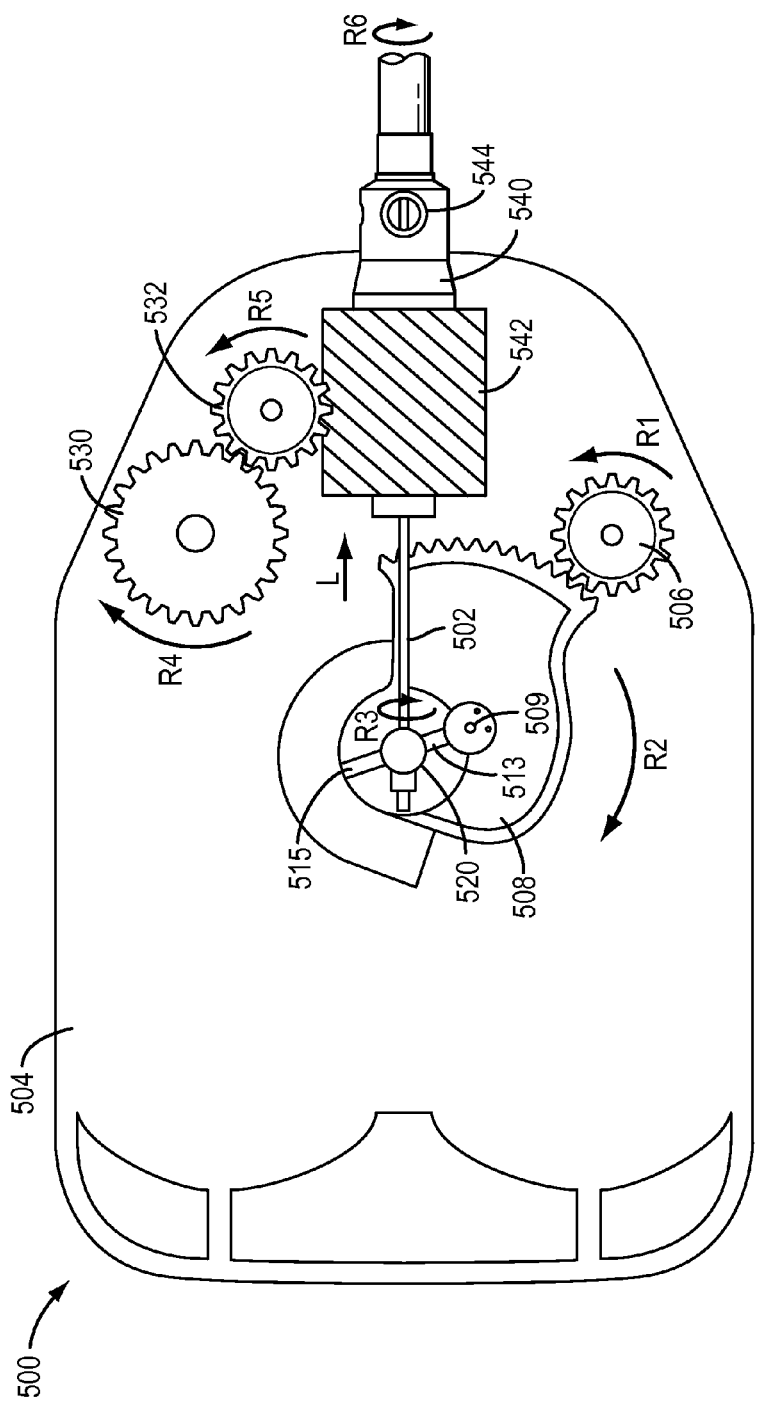
FIG. 7 is a top view of the force transmission mechanism of FIG. 5A.
Figure 8:
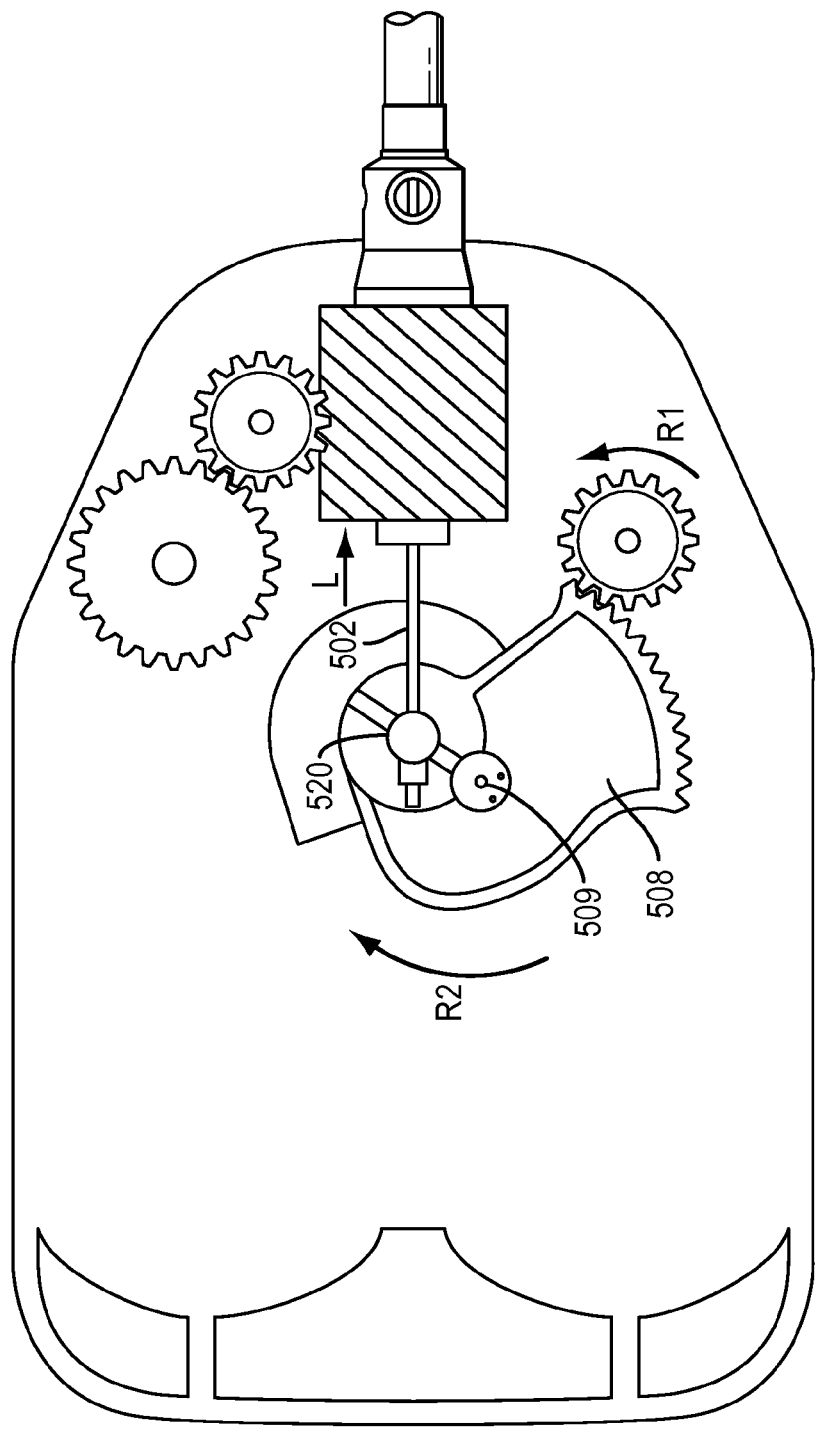
FIG. 8 is a top view of the force transmission mechanism of FIG. 7 when the push/pull drive element rod has advanced to a forward position.

The motion of a push/pull drive element rod 502, sector gear 508, and input disk 506 of a force transmission mechanism 500 is further illustrated in FIGS. 7 and 8. According to an exemplary embodiment, FIG. 7 may show a first state of a force transmission mechanism 500 and FIG. 8 may show a second state of a force transmission mechanism 500. For instance, when a surgical instrument connected to the push/pull drive element rod 502 is forceps, the first state shown in FIG. 7 may be a state in which the forceps are closed, while the second state shown in FIG. 8 may be a state in which the forceps are open. Therefore, as shown in FIG. 7, when an input disk 506 rotates in direction R1, sector gear 508 may rotate in direction R2 to cause rod 502 to advance forward in a substantially linear direction L, as shown in FIG. 8, and actuate the surgical instrument. For instance, rod 502 may be translated forward to move actuate an end effector of an instrument from a closed position to an open position.

Further, because the ball connection 520 is fixed to rod 502 and ball connection 520 is free to rotate relative to the sector gear 508, when the rod 502 is rotated in direction R3, such as when a surgical instrument (not shown) that rod 502 is connected to rotates, ball connection 520 may also rotate in direction R3 about an axis of ball connection 520 relative to the sector gear 508, as shown in FIG. 6.

According to an exemplary embodiment, a force transmission mechanism 500 may include one or more structures to cause rotation of a surgical instrument. Turning to FIG. 7, a force transmission mechanism 500 may include a second input disk 530. Second input disk 530 may be engaged with a gear 532, which in turn is engaged with a proximal end of a shaft 540 of a surgical instrument, as shown in FIG. 7. The shaft 540 may include or otherwise be engaged to a shaft roll gear 542 that is engaged with gear 532. According to an exemplary embodiment, shaft 540 may include a flush fluid entry port 544 at the proximal end of the instrument shaft 540. In the depicted implementation of FIG. 7, the flush fluid port 544 is made part of the assembly that couples the shaft 540 to the roll gear 542, or is otherwise a part of the portion of the shaft 540 that forms the roll gear 542. Flush fluid may be directed into the port 544 to clean components inside the shaft 540. For example, even though an actuating drive rod or cable may extend through a wipe seal at the distal end of the shaft 540, a small amount of body fluid may pass the seal and enter the inside of the shaft body.

Similar to input disk 506, second input disk 530 may couple with a force transmission disk of a carriage, such as carriage 212 of a PSM 204 to couple actuation forces from actuators 232 in PSM 204 shown in the exemplary embodiment of FIG. 2B. As a result, second input disk 530 may be rotated in direction R4, as shown in FIG. 7. Due to the rotation R4 of the second input disk 530, gear 532 may be rotated in direction R5, causing roll gear 542 and shaft 540 to rotate in direction R6 about a longitudinal axis of shaft 540, as shown in FIG. 7, due to the engagement between roll gear 542, gear 532, and second input disk 530.

Thus in one illustrative implementation, input disk 506 may actuate an end effector of a surgical instrument, such as to open and close a jaw mechanism of an end effector, while second input disk 530 may roll a shaft 540 of the surgical instrument so as to provide a roll DOF for the end effector of the surgical instrument. Because an end effector of a surgical instrument is coupled to shaft 540, the end effector is rotated when the shaft 540 is rotated. Further, because rod 502 is coupled to the end effector to actuate it, rod 502 is rotated in direction R3 when the shaft 540 is rotated in direction R6, as shown in FIG. 7. However, the ball connection 520 that couples the rod 502 to the sector gear 508 permits rotational movement of the rod 502 relative to the sector gear 508, while also converting rotational movement of the sector gear 508 into a substantially linear movement.

Figure 9A:
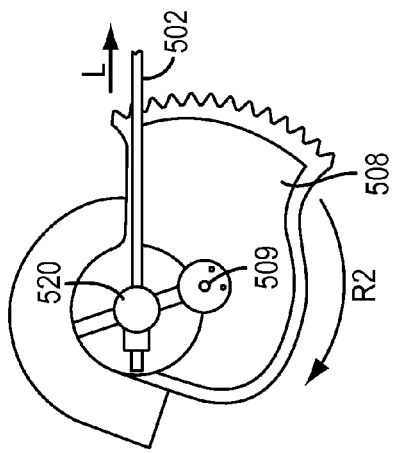
FIG. 9A is a top view of another exemplary embodiment of a sector gear and ball connection when a push/pull drive element rod is in a retracted position.
Figure 9B:
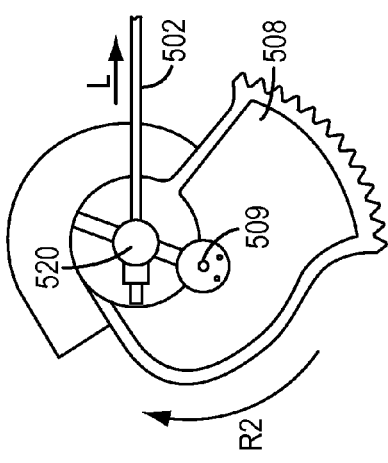
FIG. 9B is a top view of the exemplary embodiment of the sector gear and ball connection of FIG. 9A when the push/pull drive element rod has partially advanced to a forward position.
Figure 9C:
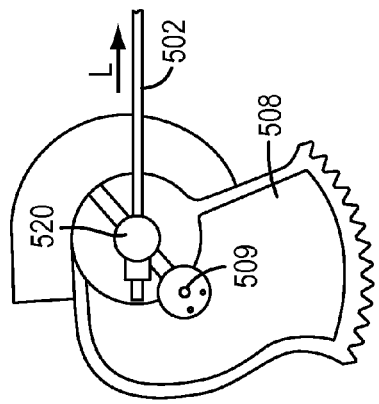
FIG. 9C is a top view of the exemplary embodiment of the sector gear and ball connection of FIG. 9A when the push/pull drive element rod has fully advanced to a forward position.

As described above, the rotational movement of a sector gear 508 may be converted into a substantially linear movement of a push/pull drive element rod 502 via a ball connection 520. When examined closely, one may determine that the motion of the ball connection 520 and portions of the rod 502 connected to the ball connection 520 and proximate to the ball connection 520 may travel through an arc as the sector gear 508 is rotated. Turning to FIG. 9A, a top view of a sector gear 508, ball connection 520, and push/pull drive element rod 502 is shown in a first, initial state when rod 502 is in a withdrawn position. As sector gear 508 rotates in direction R2 around its axis 509, ball connection 520 is carried by sector gear 508 to push rod 502 in a substantially linear direction L, as shown in FIG. 9B. The rotation of sector gear 508 may continue to advance ball connection 520 and rod 502 to a forward position, as shown in FIG. 9C.

Figure 10A:
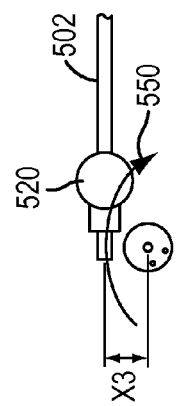
FIG. 10A is a top view illustrating the relative positions of a ball connection and a rotation axis for the sector gear illustrated in FIG. 9A.
Figure 10B:
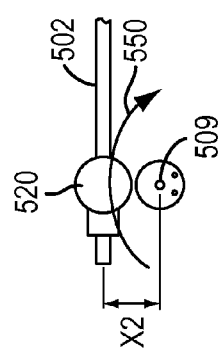
FIG. 10B is a top view illustrating the relative positions of a ball connection and a rotation axis for the sector gear illustrated in FIG. 9B.
Figure 10C:
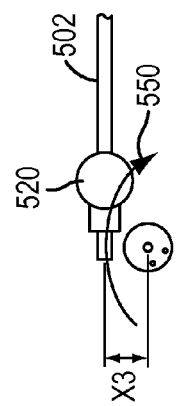
FIG. 10C is a top view illustrating the relative positions of a ball connection and a rotation axis for the sector gear illustrated in FIG. 9C.

Turning to FIG. 10A, the positions of the ball connection 520 and rod 502 are shown relative to the sector gear axis 509 for the arrangement shown in FIG. 9A. Similarly, FIG. 10B depicts the positions of the ball connection 520 and rod 502 relative to the sector gear axis 509 for the arrangement of FIG. 9B and FIG. 10C depicts the positions of the ball connection 520 and rod 502 relative to the sector gear axis 509 for the arrangement of FIG. 9C. As shown in FIGS. 10A-10C, as sector gear 508 rotates about axis 509, ball connection 520 is carried by the sector gear 508 and revolves around axis 509. Thus, ball connection 520 may travel along an arc 550 about axis 509 as the sector gear 508 rotates. This may cause a vertical distance between the ball connection 520 and the axis 509, such as from a center of ball connection 520 to axis 509, to vary, with a first distance X1 between ball connection 520 and axis 509 in FIG. 10A being less than a second distance X2 in FIG. 10B. Further, a third distance X3 shown in FIG. 10C may be less than the second distance X2 in FIG. 10B. Third distance X3 may be, for example, the same as first distance X1 or may be substantially the same. Further, a portion of the rod 502 connected to the ball connection 520, and possibly portions of the rod 502 proximate to the ball connection 520, may also travel in an arc 550 relative to axis 509.

However, due to the relatively small range of movement of the sector gear 508 and the ball connection 520 and because the end effector that is actuated by the rod 502 is located a distance away from the ball connection 520, the motion induced in the rod 502 may be considered to be a substantially linear direction. For instance, a motion induced in rod 502 proximate to the end effector of a surgical instrument may be in a substantially linear direction.

Figure 11:
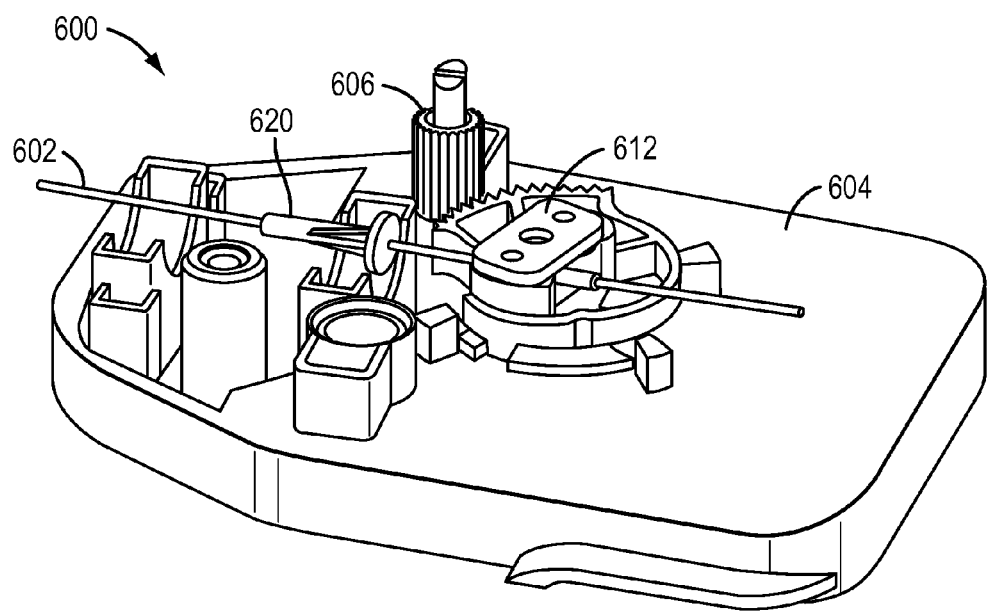
FIG. 11 is a perspective view of another exemplary embodiment of a force transmission mechanism used in a push/pull instrument design in accordance with the present teachings.

According to another exemplary embodiment, a force transmission mechanism may include a structure to support a push/pull drive element rod. Turning to FIG. 11, an exemplary embodiment of a force transmission mechanism 600 that includes a guide 620 configured to support a push/pull drive element rod 602. Guide 620 may be connected to a base 604 and may include an aperture through which rod 602 passes, as shown in the exemplary embodiment of FIG. 11. By supporting rod 602, guide 620 may advantageously reduce an unsupported length of rod 602 and may minimize or eliminate deflection or buckling of rod 602. For example, guide 620 may cut the unsupported length of rod 602 in half. As shown in the exemplary embodiment of FIG. 11, guide 620 may have a conical or substantially frusto-conical shape. Although the unsupported length of rod 602 may be reduced in comparison to rod 502 of the embodiment of FIGS. 9A-9C, rod 602 may experience a similar or same movement as rod 502, as illustrated in FIGS. 10A-10C.

Figure 12:
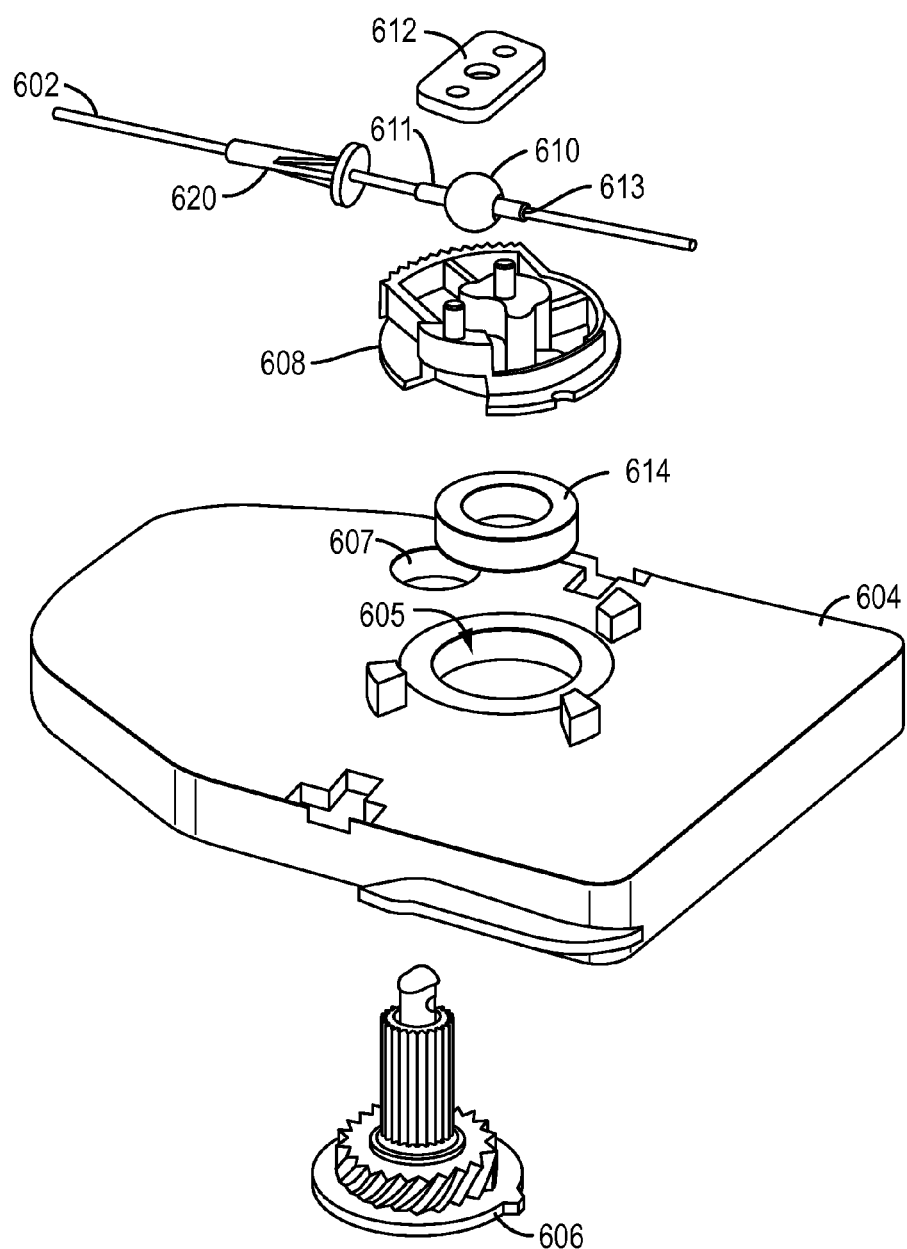
FIG. 12 is an exploded perspective view of the force transmission mechanism of FIG. 11.

As shown in FIG. 12, which shows an exploded view of the force transmission mechanism 600 of FIG. 11, the force transmission mechanism 600 may include a pocket 605 and an aperture 607 in base 604, an input disk 606, a bearing 614, a sector gear 608, a ball connection 610 with one or more fasteners 611. These features may be arranged according to the embodiments described above, such as the embodiment of FIG. 3. According to an exemplary embodiment, the force transmission mechanism 600 may further include a plate 612, as described above for the embodiment of FIG. 4.

Figure 13:
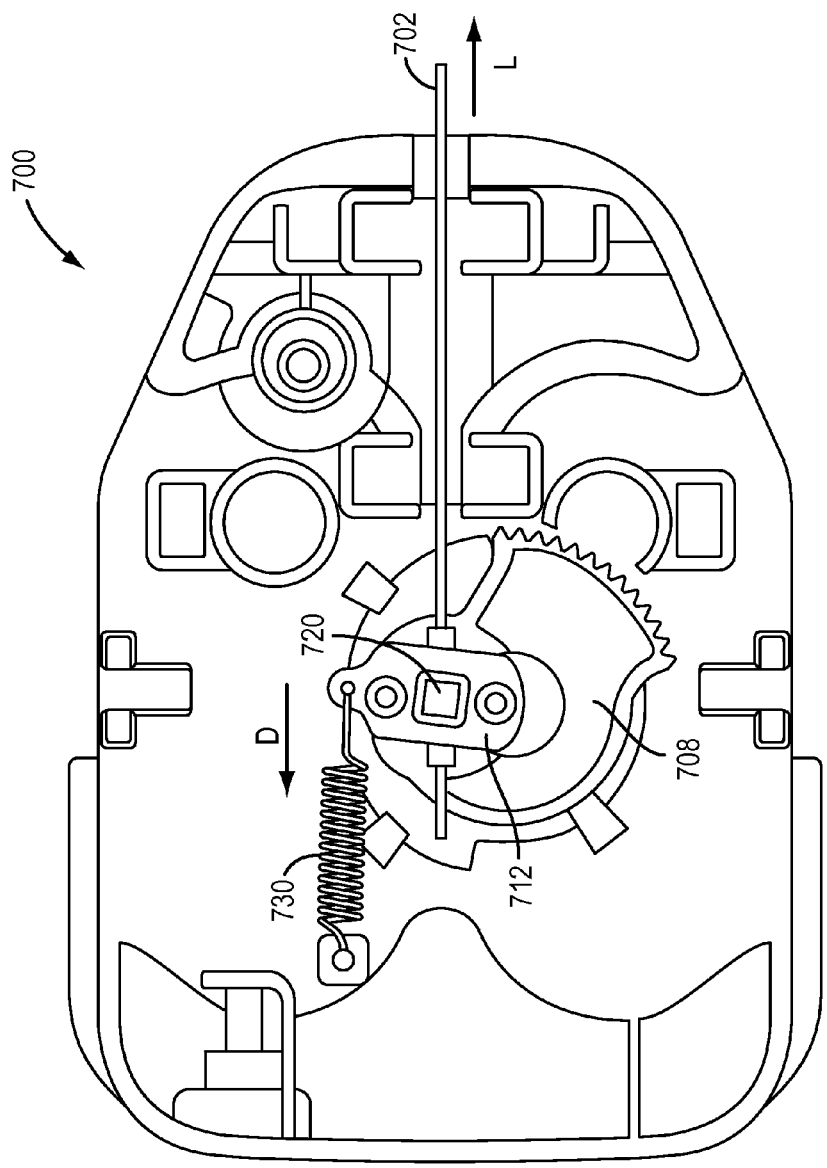
FIG. 13 is a top view of an exemplary embodiment of a force transmission mechanism that includes a biasing device.

According to an exemplary embodiment, a force transmission mechanism may include one or more devices to bias push/pull drive element rod to an initial position when a torque is not applied to a sector gear. Turning to FIG. 13, an exemplary embodiment of a force transmission mechanism 700 is shown that includes a sector gear 708 and ball connection 720 connected to a push/pull drive element rod 702. These features may be arranged according to the embodiments described above, such as the embodiment of FIG. 3. According to an exemplary embodiment, the force transmission mechanism 700 may further include a plate 712, as described above for the embodiment of FIG. 4.

Force transmission mechanism 700 may further include a biasing device 730 to exert a force to bias sector gear 708, such as in direction D shown in the exemplary embodiment of FIG. 13. For instance, when an end effector of a surgical instrument is forceps or shears, biasing device 730 may function to pull rod 702 in direction D so that the forceps or shears are actuated to a closed configuration (e.g., a biased position). By biasing an end effector to a closed position (e.g., biased position), the biasing device 730 may advantageously prevent or minimize a back side of the end effector from striking a cannula (not shown) during withdrawal or removal of a surgical instrument through the cannula. For instance, the backs of an end effector, such as the jaws of forceps, could have an insulative coating that could be damaged if the jaws strike the cannula during withdrawal of the forceps. By biasing the jaws to a closed configuration with a biasing device, damage to the coating can be minimized or avoided.

According to an exemplary embodiment, biasing device 730 may be a spring. The spring force may be selected based on the intended application of the end effectors, and may, for example, to chosen to minimize friction or to maximize grip force. The spring may exert a force in a range of, for example, approximately half a pound to approximately 3 pounds. In another example, a spring may exert a force in a range of, for example, approximately half a pound to approximately 8 pounds. According to another exemplary embodiment, a biasing force of a spring may be in a range of, for example, approximately half a pound to approximately 6 pounds. According to another exemplary embodiment, a biasing force of a spring may be in a range of, for example, approximately half a pound to approximately 3 pounds. According to another exemplary embodiment, a biasing force of a spring may be in a range of, for example, approximately half a pound to approximately 2 pounds.

A spring may be selected to exert no less than approximately a half pound of force upon rod 702 because less force may not be sufficient to overcome friction and pull rod 702 in direction D shown in FIG. 13. A spring may be selected to exert no more than 2 pounds or 3 pounds so that a dissecting force of an end effector of a surgical instrument is not substantially reduced or negatively impacted. A dissecting force is a force used when the end effector placed against tissue or within a tissue gap to push tissue apart. If a biasing force is too great, the spring may prevent a rod 702 from being advanced with sufficient force to allow an end effector to provide a dissecting force. However, an instrument may be used for applications other than dissection. For instance, in the case of a needle driver, the biasing force of a spring could be used to obtain a greater amount of grip.

This may be limited by the ability of an input disk to overcome the biasing force of the spring in order to open up the end effectors of an instrument. Further, although biasing device 730 may be a spring, the biasing device is not limited to a spring and may be other types of biasing devices.

Figure 14:
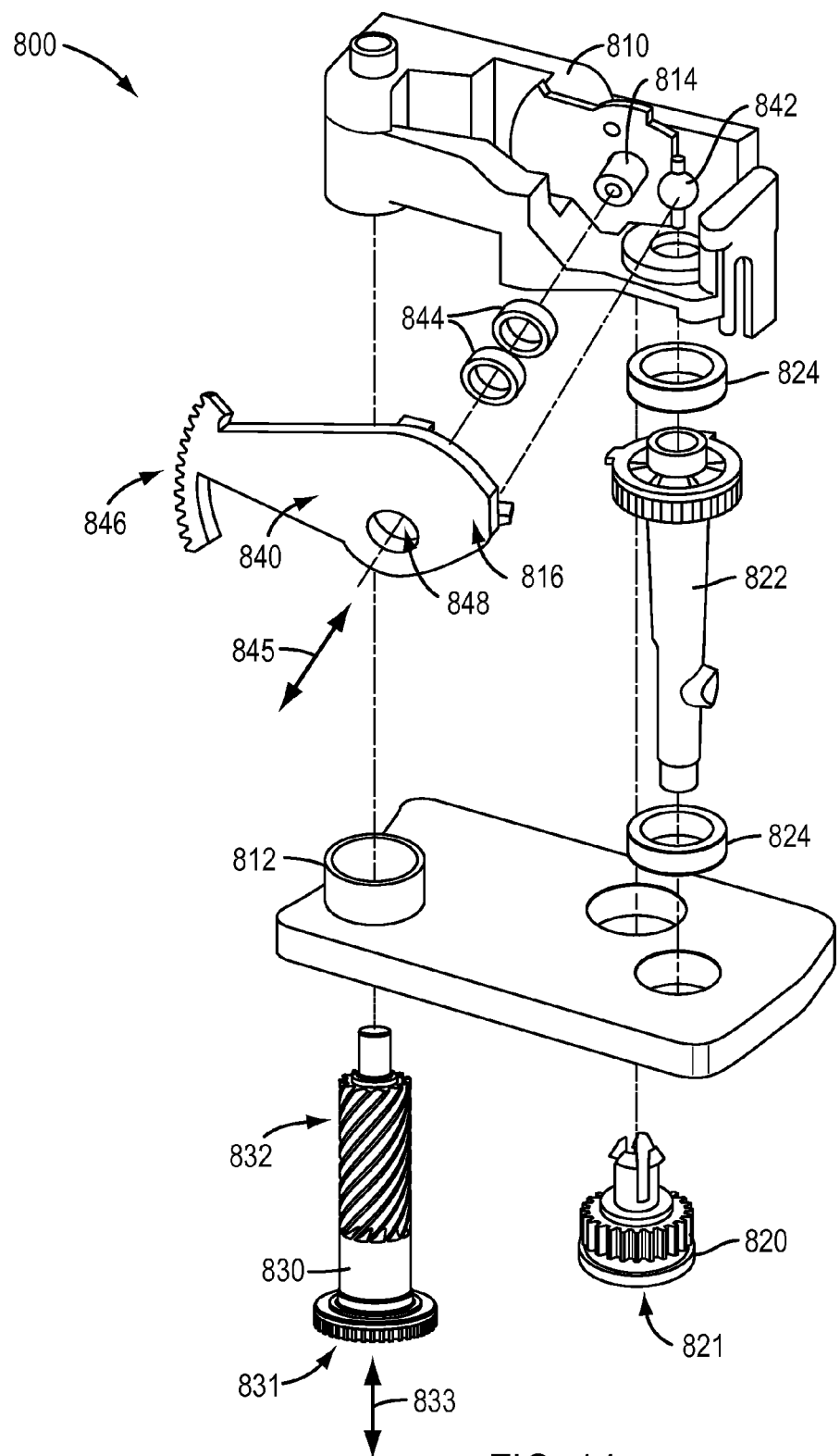
FIG. 14 is an exploded perspective view of an exemplary embodiment of a force transmission mechanism used in a push/pull instrument design.

Turning to FIG. 14, another exemplary embodiment of a force transmission mechanism 800 is shown. Force transmission mechanism 800 may include a chassis 810 and a base 812 to support features of force transmission mechanism 800. Force transmission mechanism 800 may further include a shaft roll input gear 820 that engages with a shaft roll output gear 822 to provide a rolling motion to a shaft of an instrument (not shown). For instance, a bottom portion 821 of shaft roll input gear 820 may couple with a carriage of a PSM to receive a rotational force, causing shaft roll input gear 820 to rotate, which in turn causes shaft roll output gear 822 to rotate an instrument shaft. Shaft roll input gear 820 and shaft roll output gear 822 may be supported by one or more bearings 824, as shown in the exemplary embodiment of FIG. 14.

Force transmission mechanism 800 may further include a rocker input gear 830 and a rocker member 840. Rocker member 840 may be connected to chassis 810. For instance, chassis 810 may include a projection 814 that fits through an aperture 848 of rocker member 840 so that rocker member 840 may pivot about projection 814. At least one bearing 844 may be provided to support rocker member 840 on projection 814, according to an exemplary embodiment. As shown in the exemplary embodiment of FIG. 14, at least two bearings 844 may be provided to distribute a load between rocker member 840 and projection 814.

According to an exemplary embodiment, rocker member 840 may be connected to an end effector of an instrument (not shown). As shown in the exemplary embodiment of FIGS. 14 and 15, rocker member 840 may include a ball connection 842. Ball connection 842 may be configured according to the exemplary embodiments of FIGS. 3-13 discussed above. As shown in the exemplary embodiment of FIG. 15, a push/pull drive element rod 860 coupled to an end effector of a surgical instrument may be connected to ball connection 842. Ball connection 842 may permit both rotational and translational movement of push/pull drive element rod 860, such as, for example, in translation along direction 872 and rotation in direction 874 shown in the exemplary embodiment of FIG. 15.

Figure 15:
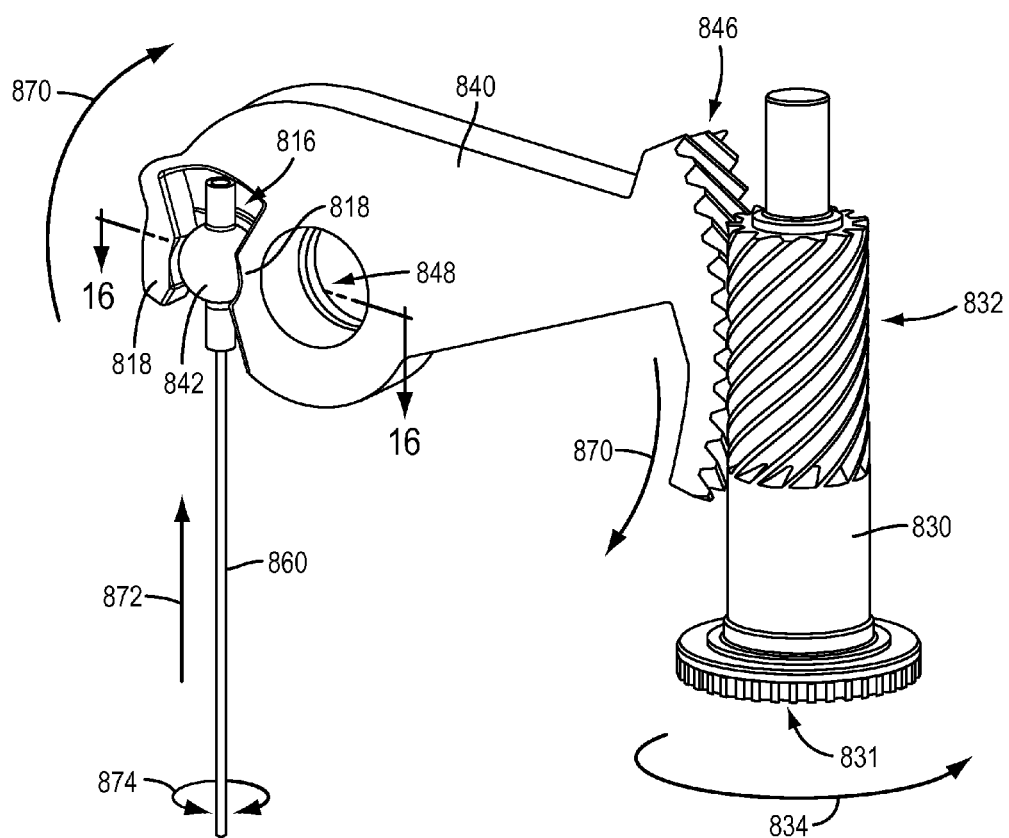
FIG. 15 is a perspective view of a portion of a force transmission mechanism used in a push/pull instrument design.
Figure 16:
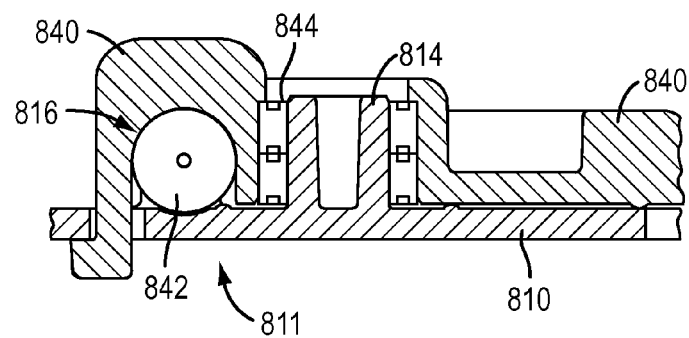
FIG. 16 is a cross-sectional view along line 16-16 of FIG. 15, with a chassis shown.
Figure 17:
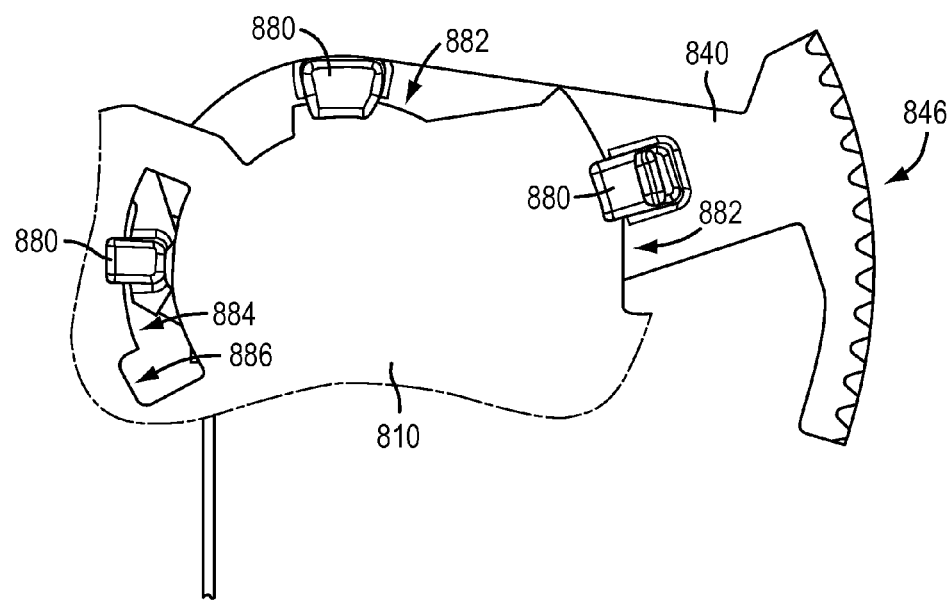
FIG. 17 is a rear view of a chassis and rocker member of a force transmission mechanism, according to an exemplary embodiment.

As shown in FIG. 15, ball connection 842 may be received within a recess or socket 816 of rocker member 840 to connect rocker member 840 and ball connection 842 to one another. Socket 816 may be configured according to the exemplary embodiments of FIGS. 3-13 discussed above. For example, rocker member 840 may include one or more wall portions 818 to facilitate fastening ball connection 842 within socket 816. In another example, wall portions 818 may be projections (not shown) that extend into socket 816 to facilitate fastening ball connection 842 within socket 816. As a result, ball connection 842 may snap fit into socket 816. According to an exemplary embodiment, a portion 811 of chassis 810 may cover at least a portion of socket 816 and ball connection 842, as shown in FIG. 16, to assist in holding ball connection 842 within socket 816. Rocker member 840 may be connected to chassis 810, for example, via one or more hooks 880, on one of rocker member 840 and chassis 810, with the hooks 880 engaging with guide surfaces 882, 884, as shown in the exemplary embodiment of FIG. 17. Guide surfaces 882 may be convex and guide surface 884 may be concave, as shown in FIG. 17. Rocker member 840 and chassis 810 may be assembled together, for example, by engaging one or more hooks 880 with guide surface(s) 882 and by inserting a hook 880 through a slot 886 in chassis 810, according to an exemplary embodiment. Subsequently, rocker member 840 may be rotated in a counter-clockwise direction in FIG. 17 to engage hook 880 with guide surface 884. During operation of a surgical instrument, hooks 880 remain engaged with guide surfaces 882, 884.

According to an exemplary embodiment, rocker input gear 830 may input a force to rocker member 840 to actuate an end effector of an instrument. For instance, a bottom portion 831 of rocker input gear 830 may couple with a carriage of a PSM to receive a rotational force to rotate rocker input gear 830, such as around axis 833, which may in turn be input to rocker member 840. According to an exemplary embodiment, rocker input gear 830 may engage with rocker member 840 via gearing. For instance, rocker input gear 830 may include a section of helical gear teeth 832 that engage with a sector gear portion 846 of rocker member 840, as shown in FIGS. 14 and 15. Thus, when rocker input gear 830 is rotated in direction 834, such as around axis 845, as shown in the exemplary embodiment of FIG. 15, helical gear teeth 832 urge sector gear portion 846 in direction 870, which in turn causes the remainder of rocker member 840 to pivot around projection 814 (not shown in FIG. 15) within aperture 848 in direction 870. Further, because ball connection 842 is connected to rocker member 840 within socket 816, ball connection 842 is moved along with rocker member 840, causing push/pull drive element rod 860 to be pulled substantially along direction 872 to actuate an end effector of a surgical instrument. According to an exemplary embodiment, rotation axis 845 of rocker member 840 and rotation axis 833 of rocker input gear 830 may be substantially perpendicular to one another.

The force transmission mechanisms described in the embodiments above may be made from various materials. For instance, gears, including sector gears and rocker members, may be made, for example, from autoclavable polyetherimide (PEI), such as Ultem®, so that the gears may be cleaned and sterilized and may be manufactured inexpensively. Such gears may further include glass fibers to add strength and rigidity. For instance, PEI may include glass fibers in a range of, for example, approximately 5% to approximately 15%. In another example, PEI may include glass fibers in a range of approximately 10%. The gears may include polytetrafluoroethylene (PTFE), such as Teflon®, to reduce friction between the gear and other parts, such as friction between a sector gear and a ball connection. For instance, PEI may include PTFE in a range of, for example, approximately 10% to approximately 20%. In another example, PEI may include PTFE in a range of approximately 15%.

According to an exemplary embodiment, a ball connection may be made of a metal or metal alloy. For instance, a ball connection may be made of stainless steel. Because a ball connection may be made of metal, the ball connection may serve as an electrical contact, such as when an electrical signal or current may be sent along a push/pull drive element rod. A push/pull drive element rod may be a metal or metal alloy, such as stainless steel, although other materials may be used, such as composites, fiberglass, electrically insulative materials, and carbon. According to an exemplary embodiment, an input disk may be made of aluminum or an aluminum alloy overmolded with plastic.

By providing a force transmission mechanism with a ball connection to connect a gear and a push/pull drive element rod, the number of parts may be minimized and the cost of manufacturing the force transmission mechanism may be advantageously reduced while permitting the connection between the gear and the rod to provide both rotational movement and translational movement of the rod. Further, the gear may be structured to move through a limited amount of space within the force transmission mechanism. As a result, relatively little open space is required within the force transmission mechanism to accommodate the rotational movement of the gear.

This description and the accompanying drawings that illustrate exemplary embodiments should not be taken as limiting. Various mechanical, compositional, structural, electrical, and operational changes may be made without departing from the scope of this description and the invention as claimed, including equivalents. In some instances, well-known structures and techniques have not been shown or described in detail so as not to obscure the disclosure. Like numbers in two or more figures represent the same or similar elements. Furthermore, elements and their associated features that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly.

Further modifications and alternative embodiments will be apparent to those of ordinary skill in the art in view of the disclosure herein. For example, the systems and the methods may include additional components or steps that were omitted from the diagrams and description for clarity of operation. Accordingly, this description is to be construed as illustrative only and is for the purpose of teaching those skilled in the art the general manner of carrying out the present teachings. It is to be understood that the various embodiments shown and described herein are to be taken as exemplary. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the spirit and scope of the present teachings and following claims.

It is to be understood that the particular examples and embodiments set forth herein are non-limiting, and modifications to structure, dimensions, materials, and methodologies may be made without departing from the scope of the present teachings.

Other embodiments in accordance with the present disclosure will be apparent to those skilled in the art from consideration of the specification and practice of the invention disclosed herein. It is intended that the specification and examples be considered as exemplary only, with a true scope and spirit being indicated by the following claims.

What is claimed is:

1. A force transmission mechanism for a teleoperated surgical instrument, comprising:
   a gear configured to be driven by a drive input mechanism;
   a push/pull drive element configured to transmit force to actuate an end effector of the surgical instrument; and
   a ball element operatively coupling the gear and the push/pull drive element,
   wherein driven motion of the gear is transmitted to the push/pull drive element to actuate the end effector.

2. The force transmission mechanism of claim 1, wherein the push/pull drive element is a push/pull drive element rod.

3. The force transmission mechanism of claim 1, wherein the ball element operatively couples the gear and the push/pull drive element to convert a rotational motion of the gear to a substantially linear motion of the push/pull drive element.

4. The force transmission mechanism of claim 3, wherein the ball element is freely rotatable relative to the gear about an axis of the ball element.

5. The force transmission mechanism of claim 1, wherein the gear is a sector gear.

6. The force transmission mechanism of claim 5, wherein the sector gear includes a socket and wherein the ball element is received in the socket.

7. The force transmission mechanism of claim 5, wherein the drive input mechanism comprises an input gear engaged with the sector gear, wherein a rotation axis of the input gear and a rotation axis of the sector gear are substantially parallel to one another.

8. The force transmission mechanism of claim 5, wherein the drive input mechanism comprises an input gear engaged with the sector gear, wherein the sector gear is part of a rocker member, wherein a rotation axis of the input gear and a rotation axis of the rocker member are substantially perpendicular to one another.

9. The force transmission mechanism of claim 1, wherein the push/pull drive element passes at least partially through the ball element.

10. The force transmission mechanism of claim 1, wherein the drive input mechanism comprises an input disk configured to engage with a servomechanism of a teleoperated surgical system.

11. The force transmission mechanism of claim 10, further comprising a second input disk configured to operatively couple with a shaft of the surgical instrument to impart a rotational movement to the shaft about a longitudinal axis of the shaft.

12. The force transmission mechanism of claim 1, further comprising a plate, wherein the ball element is located between the gear and the plate.

13. The force transmission mechanism of claim 1, further comprising a biasing device to bias the gear and the push/pull drive element to a biased position.

14. The force transmission mechanism of claim 13, wherein the biasing device is a spring that biases the gear and the push/pull drive element to the biased position.

15. The force transmission mechanism of claim 1, wherein the gear is directly connected to the ball element and the ball element is directly connected to the push/pull drive element.

16. The force transmission mechanism of claim 1, wherein the gear partially surrounds the ball element.

17. A force transmission mechanism for a teleoperated surgical instrument, comprising:
a gear;
a push/pull drive element configured to transmit force to actuate an end effector of the surgical instrument and to rotate with a shaft of the surgical instrument when the shaft is rotated by the force transmission mechanism; and
a connection element operatively coupling the gear and the push/pull drive element, wherein the connection element is configured to convert rotational movement of the gear to a substantially linear movement of the push/pull drive element, wherein the connection element is configured to rotate with the push/pull drive element and relative to the gear, and wherein the connection element is configured to move along an arc in response to rotation of the gear.

18. The force transmission mechanism of claim 17, further comprising a drive input disk operatively coupled with the gear to impart rotational movement to the gear.

19. The force transmission mechanism of claim 17, wherein the push/pull drive element comprises a rod.

20. The force transmission mechanism of claim 17, wherein the connection element comprises a ball element.

21. The force transmission mechanism of claim 17, further comprising a guide aperture through which the push/pull drive element extends from the force transmission mechanism to the shaft of the teleoperated surgical instrument.

22. The force transmission mechanism of claim 17, wherein the gear is a sector gear.

23. A surgical instrument for a teleoperated surgical system, comprising:
a shaft;
an end effector disposed at a distal portion of the shaft; and
a force transmission mechanism disposed at a proximal portion of the shaft, the force transmission mechanism comprising:
an input disk;
a sector gear engaged with the input disk, the input disk being configured to impart rotational movement to the sector gear;
a push/pull drive element extending along the shaft to the end effector, wherein the push/pull drive element is configured to transmit force to actuate the end effector; and
a connection element operatively coupling the sector gear and the push/pull drive element to convert rotational movement of the sector gear to a substantially linear movement of the push/pull drive element to actuate the end effector;
wherein the connection element is configured to rotate with the push/pull drive element and relative to the sector gear.

24. The surgical instrument of claim 23, wherein the force transmission mechanism further comprises a second input disk, and wherein the second input disk is configured to impart a rotational movement to rotate the shaft of the surgical instrument.

* * * * *